United States Patent [19]

Williams et al.

[11] Patent Number: 4,915,913
[45] Date of Patent: Apr. 10, 1990

[54] MEDICAL STERILIZER DEVICE WITH IMPROVED LATCH MECHANISM

[75] Inventors: Edward S. Williams, Burke, Va.; John R. Herzog, Sacramento, Calif.

[73] Assignee: Genesis Medical Corporation, Cleveland, Ohio

[21] Appl. No.: 893,647

[22] Filed: Aug. 6, 1986

Related U.S. Application Data

[63] Continuation-in-part of Ser. No. 612,928, May 22, 1984, abandoned.

[51] Int. Cl.4 ............................................. A61L 2/26
[52] U.S. Cl. ............................ 422/119; 220/87; 220/324; 292/247; 422/297; 422/300; 422/310; 436/1
[58] Field of Search .............. 422/297, 300, 310, 119; 436/1; 292/247; 220/324, 87

[56] References Cited

U.S. PATENT DOCUMENTS

| | | | |
|---|---|---|---|
| 2,739,003 | 3/1956 | Clarke | 292/247 X |
| 2,755,920 | 7/1956 | Weckman | 220/315 X |
| 3,030,137 | 4/1962 | Cheney | 292/247 X |
| 3,394,955 | 7/1968 | Martin | 292/113 |
| 3,454,189 | 7/1969 | Lauterbach . | |
| 3,561,918 | 2/1972 | Ray . | |
| 3,704,906 | 12/1972 | Abercrombie | 292/247 |
| 3,936,082 | 2/1976 | Swanson . | |
| 4,022,324 | 5/1977 | Schuster . | |
| 4,098,577 | 7/1978 | Halpern | 436/1 |
| 4,135,868 | 1/1979 | Schainholz | 422/300 |
| 4,181,333 | 1/1980 | Stelma | 292/113 X |
| 4,267,939 | 5/1981 | Perrett et al. | 220/318 |
| 4,331,257 | 5/1982 | Taschner | 220/324 |
| 4,382,063 | 5/1983 | Romito et al. | 436/1 X |
| 4,416,417 | 11/1983 | Sanderson et al. . | |
| 4,562,047 | 12/1985 | Sestak et al. | 422/300 |
| 4,661,326 | 4/1987 | Schainholz | 422/297 X |
| 4,671,943 | 6/1987 | Wahlquist | 422/300 |

FOREIGN PATENT DOCUMENTS

| | | |
|---|---|---|
| 2207339 | 9/1973 | Fed. Rep. of Germany . |
| 15572 | 8/1912 | France . |
| 2375869 | 7/1978 | France . |
| 164675 | 10/1938 | Switzerland . |

*Primary Examiner*—Barry S. Richman
*Assistant Examiner*—Jill Johnston
*Attorney, Agent, or Firm*—Banner, Birch, McKie & Beckett

[57] ABSTRACT

The present application is directed to medical sterilizer device with an improved latch mechanism and method and, more particularly, to a new and improved sterilization device in the form of a sterilizer case of medical applications relative to the use of instrument sterilization and storage. The case of the invention provides an effective storage container and method for sterilizing medical instruments and/or equipment by fluid (gas or steam) techniques.

7 Claims, 9 Drawing Sheets

MEDICAL STERILIZER DEVICE WITH IMPROVED LATCH MECHANISM

This application is a continuation-in-part of Application Ser. No. 612,928 filed May 22, 1984, now abandoned.

TECHNICAL FIELD

The present application relates to a medical sterilizer device and method and, more particularly, to a new and improved sterilization device in the form of a sterilizer case with an improved latch mechanism for medical applications relative to the use of instrument sterilization and storage. The case of the invention provides an effective storage container and method for sterilizing medical instruments and/or equipment by fluid (gas or steam) techniques.

BACKGROUND OF THE INVENTION

It has been known to provide various types of containers for use in the medical field for the sterilization and subsequent storage of medical instruments. Such prior containers have sought to solve recognized problems relating to a durable leak-proof construction, effective sterilization fluid transmission (i.e. gas or steam penetration), positive and tamper-effective securement of the case when in its closed position for storage and ready usage which assures that the contents of the case remain sterile until the case is opened. Also, there has been a need to improve the wire (metal) mesh basket unit which is detachably supported within the case for holding the instruments to be sterilized.

SUMMARY OF THE INVENTION

The present invention includes a new and improved structure for a medical sterilization device and method which embodies a container or case which has a closeable and hermetically sealable cover. The cover and bottom of the case are perforated for fluid (gas or steam) sterilization, and the cover includes new and improved latch mechanism which affords tamper-evident control and reduces the risk of sterile gown contamination when removing the basket assembly so as to assure instrument sterilization. In the invention, the case is adapted to receive a new and improved instrument basket which is of a cross-hatch construction, as distinguished from a woven construction, which increases the strength of the basket and reduces the possibility of instruments becoming caught in the mesh. More specifically, it will be recognized hereinafter that the present invention incorporates a new and novel construction for a sterilization and storage case which provides an effective solution to problems of prior known devices.

The case of the present invention has a top and bottom which are rivet-free. Prior known containers which do not have a rivet-free construction of the top and bottom components are subject to corrosion and rusting. The present invention has an internal riveted hardware parts to loosen. The rivet-free construction of the present invention provides all necessary internal supports for filter barrier-retention plates and maximizes the cleaning efficiency of the device by eliminating hard to clean surface areas.

The present invention also incorporates a proof-positive "open or closed" cam-lock lever assembly, distinct and separate from the latch mechanisms, which fastens under indented or recessed ridge portions provided in the cover and bottom sections of the case. A protective inner-plate member is provided which has perforations staggered in off-set relation to perforations provided in the cover so as to protect against spills and punctures. One or more retention plate members are provided with a compression groove that matches a corresponding groove in the cover so as to provide a "squeeze-seal" around the entire periphery of the barrier (filter) material.

The case incorporates a tamper-evident control system. The system includes a disposable indicia element made from a polymeric material which is automatically severed when the cover latch is opened. This locking element includes an indica portion which incorporates a heat responsive material which selectively changes color when processed. This color change automatically and accurately verifies whether or not the case and hence, the instruments contained therein, have been sterilized. Accordingly, this tamper-evident construction provides a dual "fail-safe" system to determine and verify whether or not the case has been opened for whatever cause, and if opened, whether the contents of the case has been sterilized.

The case of the present invention further includes an improved latch mechanism mounted on opposed sides of the container with each of the latch mechanisms being mounted in a cantilevered relation from a support bar member detachably connected in laterally spaced relation relative to the sidewall of said case. The latch mechanism includes a hinge plate member hinged to the support bar member. The hinge plate member is pivotally mounted on a latch plate member which, in turn, includes an integral hook-like flange portion adapted for gripping engagement with a peripheral recessed groove provided in the cover member. A first retention member extends outwardly from the support bar member and is adapted to be received through an opening provided in the hinge plate member, and a second retention member is mounted on the hinge plate member and adapted for axial alignment with the first retention member for receiving the indicia element inserted therein. The indicia element normally holds the hinge plate member and latch plate member in closed relation to the cover member and is adapted to be automatically severed upon pivotal movement of the hinge plate member relative to the support bar member to enable pivotal movement of the latch plate member relative to the hinge plate member.

In a second preferred embodiment of the sterilizer device with a "double-action" latch mechanism, the latch is formed of a cover latch plate pivotally mounted on its upper edge to a support bar member affixed to the cover and a bottom latch plate pivotally mounted at its upper edge to a support bar member affixed to the sidewall of the case. The cover latch plate is generally J-shaped, with the curved portion forming the lower edge of the plate opposite the pivot axis. The bottom latch plate has a hook portion configured to engage with the curved portion of the cover latch plate when the bottom latch plate is rotated downwardly and, thus, secures the cover in a sealed and locked position. The latch construction in accordance with the second preferred embodiment of the present invention provides for increased compression of the resilient seal disposed between the cover and the case and, hence, provides a tigher seal than previously used latch mechanisms.

After the latch is placed in its closed position, the indicia element is inserted in a guide slot. When the head and barbs extend into a hole formed in the bottom latch plate to hold the latch plates in a normally closed position, the barbs expand and the indicia element cannot be removed, without being severed. Thus, the indicia element provides an indication that the seal has been broken and the contents of the case contaminated.

The cover latch plate has a longitudinal slot which provides space for the operators fingers so that it is easier for the operator to open the latch. The slot also provides a convenient carrying handle for the cover. Additionally, the configuration of the two latch plates provides that they lie substantially flat against the sidewalls of the case, thus reducing the possibility of steril gown contamination, for example, by a scrub nurse while removing the basket.

The case of the present invention includes a perforated protective plate member which can be utilized either with a perforated cover or perforated bottom, the protective plate member includes a plurality of perforations which are oriented in off-set relationship in respect to the perforations in the cover and the bottom of the case so as to prevent the inadvertent ingress of objects and dust into the interior of the case thereby to prevent damage or puncture to a layer of absorbent material carried by barrier plate members, and to prevent inadvertent ingress of material into the interior of said case by spillage or the like. In a preferred form, the protective plate members are constructed and arranged with a least one area so as to correspond to one of the perforations in the cover or bottom of the case to permit visual inspection through the cover or bottom to detect the presence or absence of the layer of absorbent material and/or to observe the interior of the case in the absence of the layer of absorbent material.

The present invention also provides a method for the sterilization of medical instruments or the like. The method includes providing a sterilizer container for such medical instruments, sterilizing such instruments in such container, locking such container in a closed condition for purposes of storage, and providing the closed container with a tamper-evident means including a severable element which automatically indicates whether said container has been previously opened. Such element incorporates a chemically heat activatable indicia material to automatically indicate whether the container has been sterilized by a particular type of sterilizing fluid.

Other advantages and objects of the present invention will be made apparent upon consideration of the following description and claims when taken in conjunction with the following drawings.

DETAILED DESCRIPTION OF THE PREFERRED EMBODIMENTS

Figure 1:
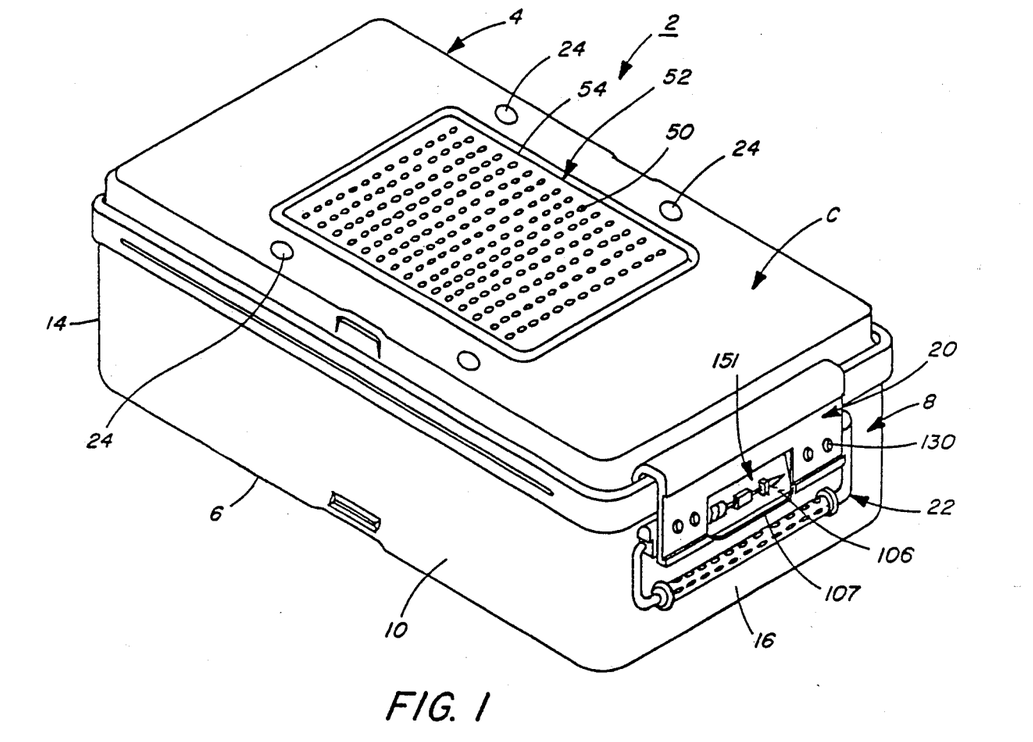
FIG. 1 is a generally perspective view illustrating the sterilizer case device made in accordance with a first preferred embodiment of the present invention.
Figure 2:
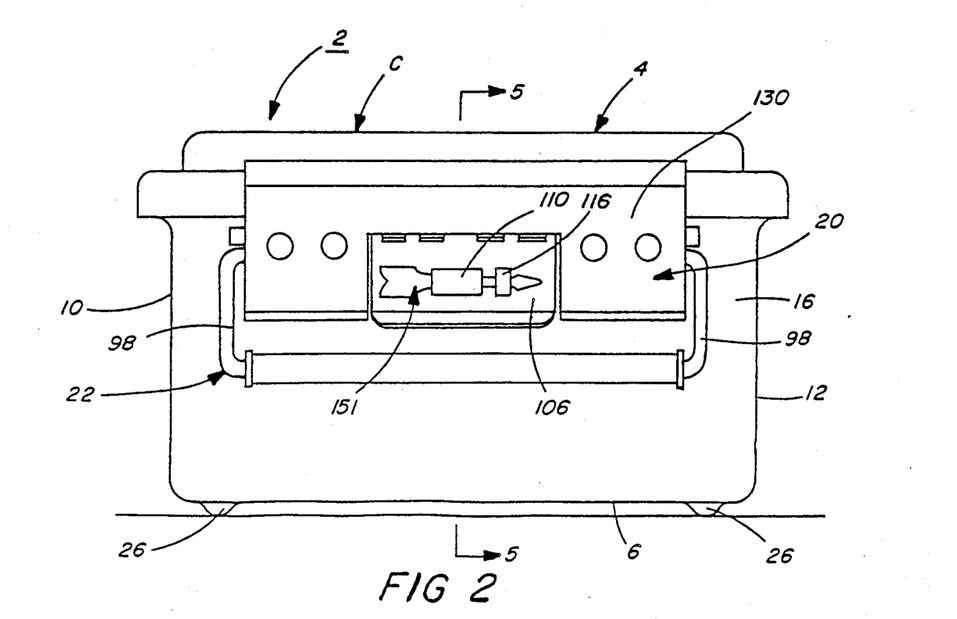
FIG. 2 is an end elevation view of the sterilizer case device illustrated in FIG. 1.
Figure 3:
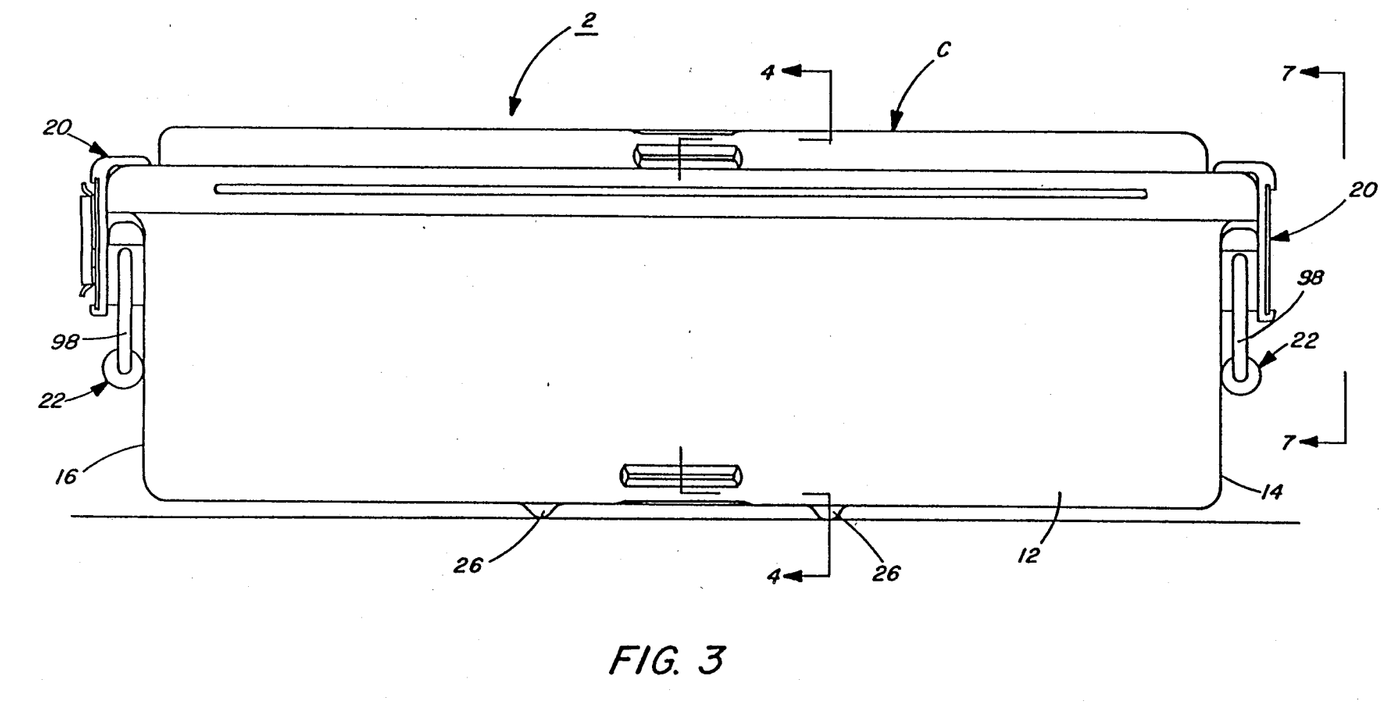
FIG. 3 is a side elevation view of the sterilizer case device illustrated in FIG. 1.

Referring again to the drawings and in particular to FIGS. 1, 2, and 3, there is illustrated the sterilizer device, designated generally at 2, made in accordance with the present invention. As shown, the device includes a polygonal (e.g. rectangular or square) container or case 4 defined by a bottom 6 and a continuous sidewall 8 which includes a pair of opposite disposed sides 10 and 12, and a pair of opposite disposed ends 14 and 16. The case 4 is adapted to be closed by a detachable cover member C. The cover member, in turn, is detachably locked to the body of the case 4 by a pair of oppositely disposed latch mechanisms 20 which are of substantially identical construction. Each latch mechanism 20 includes a handle assembly 22 for transporting the case. The cover of the case may be provided with a series of indentations 24 to receive therein correspondingly shaped boss elements 26 to facilitate vertical self-stacking of a multiplicity of such case members in the stored condition.

Figure 4:
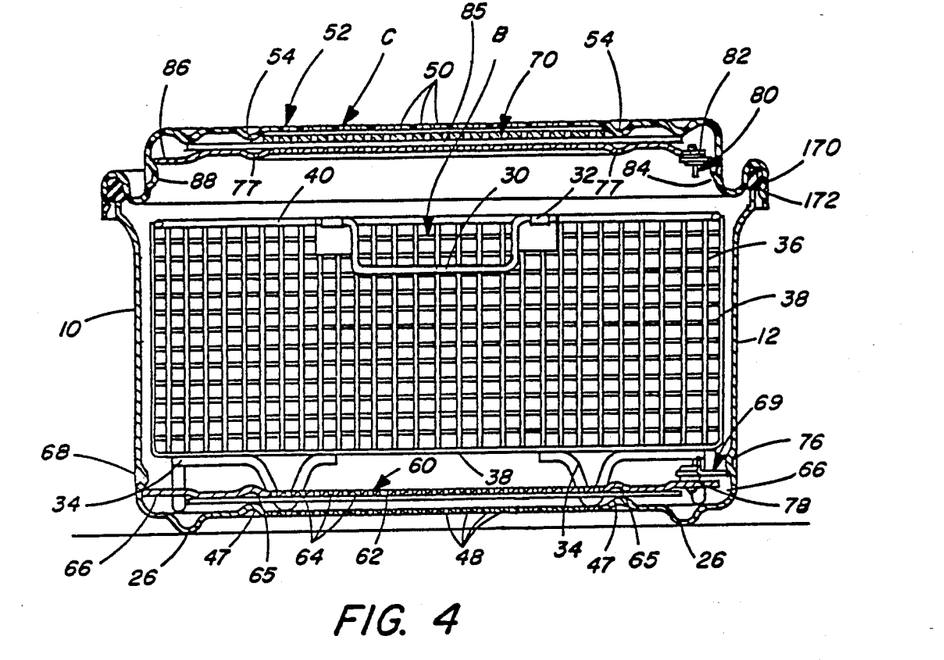
FIG. 4 is a vertical section view taken along the line 4—4 of FIG. 3.
Figure 5:
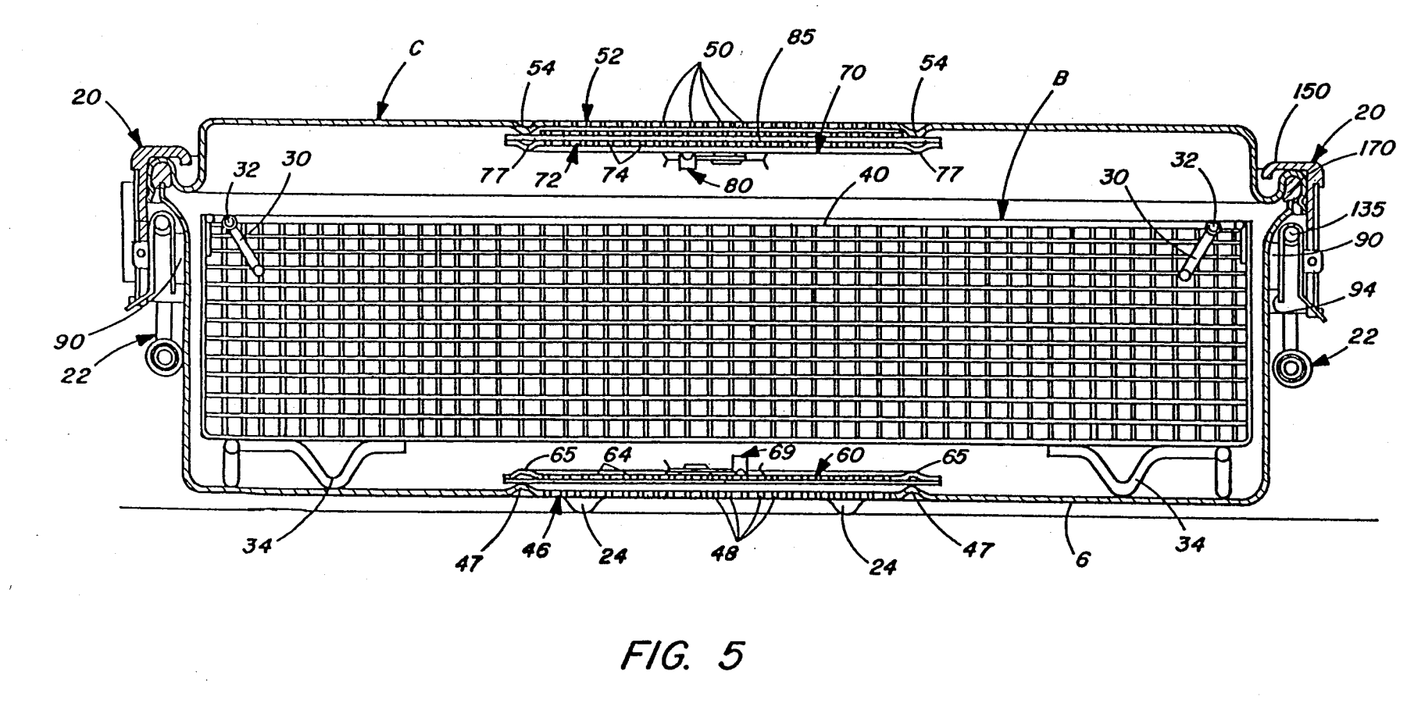
FIG. 5 is a vertical section view taken along the line 5—5 of FIG. 2.
Figure 6:
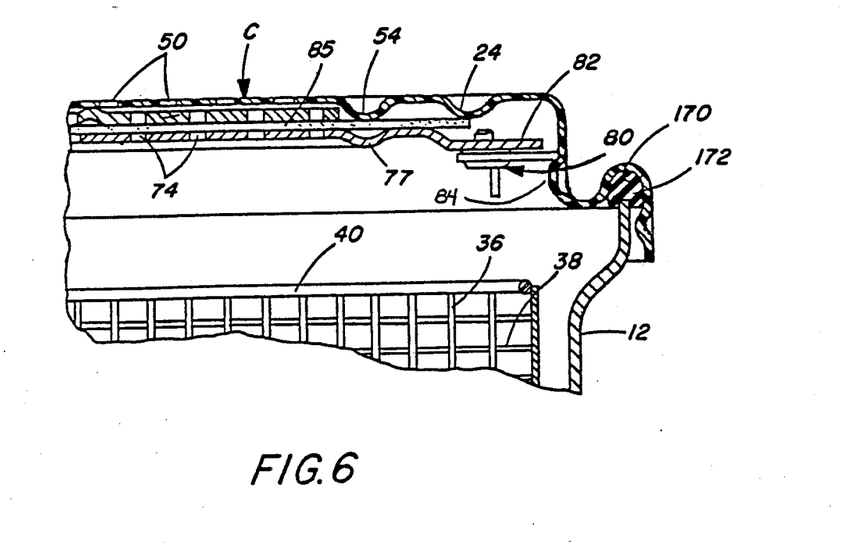
FIG. 6 is an enlarged, fragmentary vertical section view illustrating the seal construction between the case and the detachable cover.
Figure 7:
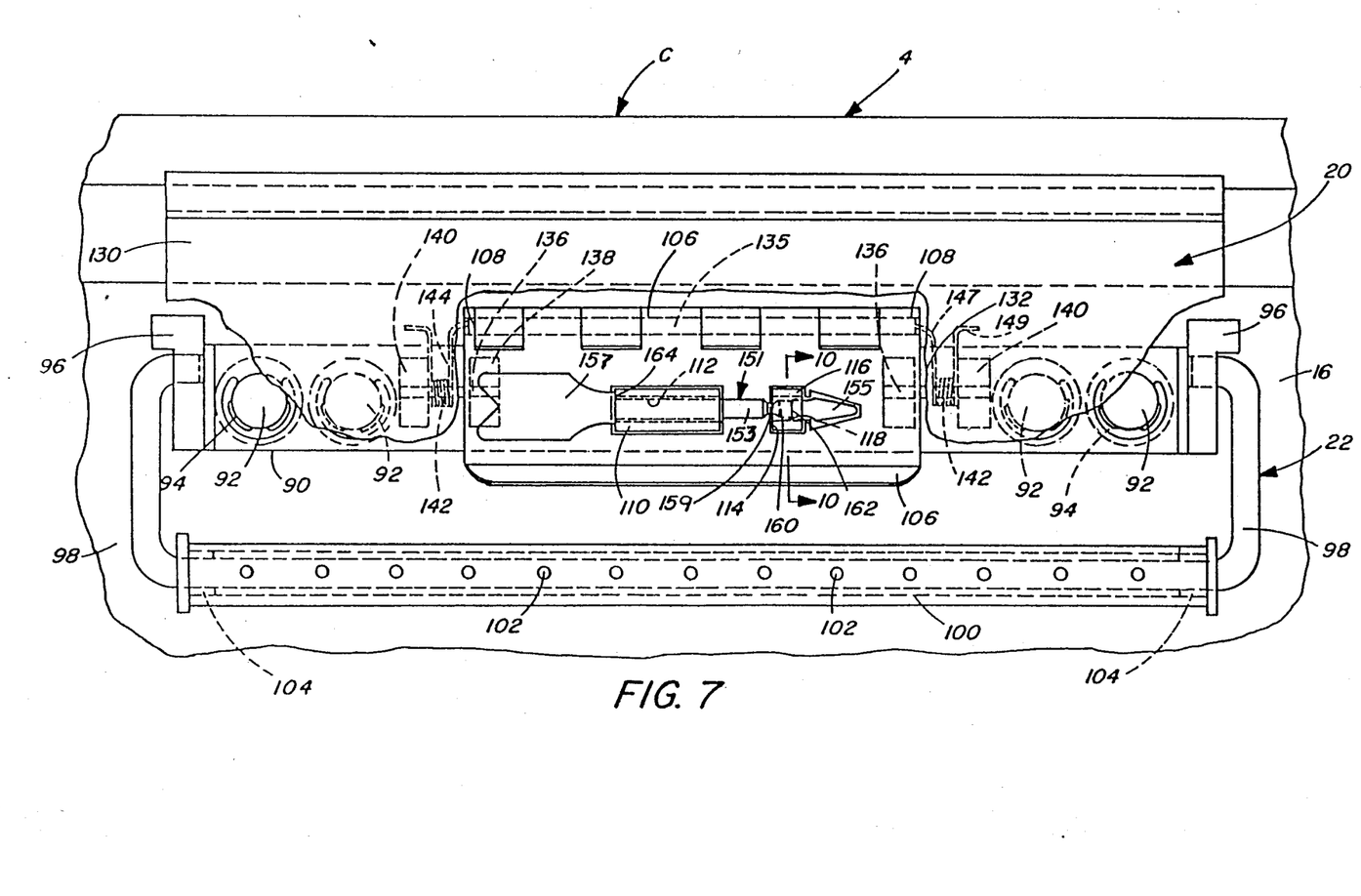
FIG. 7 is a fragmentary front elevation view on an enlarged scale illustrating the tamper-evident assembly of the latch mechanisms.

As best illustrated in FIGS. 4, 5, and 6, a basket B is removably mounted within the case and is adapted to receive therein medical instruments (not shown) to be sterilized. In this form, the basket B has a pair of handles 30 which may be pivoted, as at 32, so that the handles may be folded into the basket when not in use. The basket B has a support leg member, 34, adjacent each bottom corner for supporting the basket above the bottom 6 of the case. In the invention, the basket B is preferably made from stainless steel and is of a cross-hatch construction which is made from a plurality of spaced vertically extending wires 36 and a plurality of spaced horizontally extending wires 38. By this construction, the strength of the basket is increased and the possiblity of instruments becoming caught in the mesh is minimized. The top of the basket has a continuous upper rib member 40 which strenghtens and maintains the integrity of the basket. For example, a case having an exterior dimension of 3½" (height) by 11½" (length) by 12¼" (width) would accommodate a maximum basket size of 1¼" by 9" by 10⅝".

Figure 9:
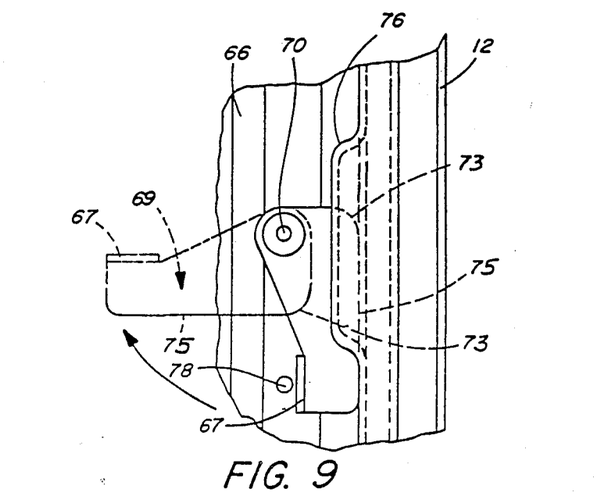
FIG. 9 is a fragmentary, top plan view of one of the interior cam-lock assemblies for retaining one of the interior barrier plate members.

Referring to FIGS. 4, 5 and 9, the bottom 6 of the case has a perforated area 46 defined by a peripheral (polygonal) recess groove 47. The perforated area is defined by a plurality of circular apertures 48 which are oriented in spaced rows so as to axially align with corresponding apertures 50 provided in a perforated area 52 in the cover C. Here again, the perforated area 52 is defined by a peripheral groove 54 formed in the cover. Preferably, the perforated areas 46 and 52 in the bottom and cover register in vertical alignment with one another in the closed condition of the cover C.

In the invention, a lower barrier plate member 60 having a peforated area 62 (FIG. 4) defined by a plurality of apertures 64 is detachably supported on the bottom 6 of the case. The perforated area 62 is defined by another recessed groove 65 which receives, in registered relation therein, the corresponding concave portion 47 defining the perforated area 46 of the bottom so as to maintain registration of the lower barrier plate 60 member relative to the bottom. Here again, the apertures 64 in the lower barrier plate member 60 are disposed for orientation with the apertures 48 in the perforated bottom. The lower barrier plate member 60 is provided adjacent to opposed ends with outwardly and slightly upwardly inclined flange portions 66 with one of the flanged portions adapted to be received under an inwardly extending ledge-like shoulder portion 68 (FIG. 4) formed from the material of the sidewall of the case. The other flange portion 66 carries a lever arm 69 (FIG. 9) having an actuating tab 67 which is pivoted, as at 70, thereto for pivotal movement about a vertical axis. The level arm 69 has a curved cam edge 73 and a linear edge 75 which is adapted to be pivoted under another ledge-like shoulder portion 76 formed from the material of the sidewall of the case. An integral boss 78 (FIG. 9) extends upwardly from the flange portion 66 and is adapted to bias the lever arm 69 upwardly as the lever arm is pivoted transversely toward the ledge-like shoulder portion 76 so as to maintain the linear edge 75 in a resilient retained engagement beneath the ledge-like shoulder portion 76 to prevent dislodgement of the lower barrier plate member 60 relative to the bottom of the case. Accordingly, the flange portions 66 of the lower barrier plate member 60 coact with the ledge-like shoulder portions 68 and 76 via the lever latch 69 so as to retain the lower barrier plate member 60 in a generally resilient, biased locking engagement relative to the bottom of the case until the lever latch is pivoted (arrow) to the open position, as illustrated in dotted line in FIG. 9.

As best seen in FIGS. 4, 5, and 6, upper barrier plate member 70 having a substantially identical construction as the lower barrier plate member is provided for detachable connection to the cover member C. Here again, the upper barrier plate member 70 has a perforated area 72 defined by a plurality of apertures 74 (FIG. 5) which are disposed for registration with the apertures 50 in the cover member C. Upper barrier plate member 70 has a peripheral recess groove 77 disposed for registration with the corresponding concave surface provided by the recess groove 54 in the cover member C, as aforesaid. Again, the upper barrier plate member 70 is retained by a lever latch arm 80 which cooperates with an integal flange 82 (FIG. 6) for retention by a ledge-like shoulder 84 formed in the interior of the sidewall of the cover member C. Similarly, the opposite flange portion 86 of the upper barrier plate member 70 (FIG. 4) is retained by a corresponding ledge-like shoulder portion 88 formed in the opposite sidewall of the cover member.

Now a barrier layer of porous filter material 85 may be disposed (FIG. 6) between the upper barrier plate member 70 and the perforated portion of the cover member C. It is contemplated that such a barrier layer could also be used between the lower barrier plate member 60 and the bottom 6 of the case. The barrier layer acts to filter deleterious material and prevent the material from entering the interior of the case during sterilization and/or upon the subsequent storage thereof, to minimize contamination of the medical instruments prior to usage thereof. These barrier layers may be comprised of an absorbent paper material which is available under the trademark PROGUARD, and is known in the field as surgicot. Of course, any other suitable material may also be used.

Now referring to a FIGS. 1–3, 5, 7 and 8 there is illustrated the novel latch mechanism 20 for the cover member C made in accordance with the first preferred embodiment of the present invention. This latch mechanism 20 (two being used) provides a double-pivot action for releaseably locking the cover member C in sealed relation in respect to the open top of the case. Each latch mechanism 20 includes a support bar member 90 fixedly attached to the outside of the case wall 16 (FIG. 7) by means of a series of polymeric stud members 92 extending from the sidewall 16 and received through openings provided in the support bar member 90. Generally C-shaped, snaprings 94 are then attached to the exposed ends of the stud members 92 for retaining the support bar member 90. In this arrangement, the latch mechanism 20 (FIG. 5) is held in the laterally spaced relation, as at 94, from the sidewall 16. The support bar member 90 has a pair of bearing members 96 (FIG. 7) disposed at the opposed ends thereof to pivotally receive the link arms 98 of the handle member 22. An elongated cooling sleeve 100 having a plurality of apertures 102 formed therein is rotatably mounted by plastic bushings 104 on the link arms 98. This apertured cooling sleeve arrangement facilitates the dissipation of heat immediately after the sterilization process and hence, enables the technician to readily transport the case for immediate use or storage, as desired.

Figure 10:
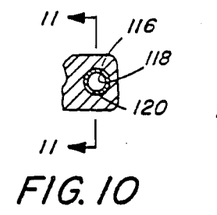
FIG. 10 is a fragmentary, vertical section view, on an enlarged scale, taken along the line 10—10 of FIG. 7.
Figure 11:
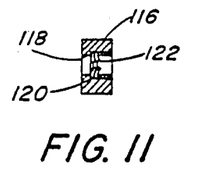
FIG. 11 is a side elevation view of FIG. 10.

Now in accordance with the invention, each latch mechanism 20 further includes a hinge plate member 106 which is hinged, as at 108, adjacent the top of the support bar member 90. This hinge is in the form of a piano-hinge construction to maximize the strength characteristics of the latch. The hinge plate member 106 has a downwardly and outwardly inclined flange portion 107 to facilitate finger gripping of the latch plate and includes an elongated retention member 110 having an axial passageway 112 (FIG. 7 and 8) extending therethrough. The hinge plate member 106 also includes an opening 114 adapted to receive therethrough a second retention member 116 (FIGS. 10 and 11) made integral with and extending outwardly from the support arm member 90. This retention member 116 has an axial passageway 118 extending therethrough which is disposed in axial alignment with the passageway 112 provided in the first retention member 110. This second retention member 116 has one or more resilient (metal) retainer rings 120 (FIGS. 10 and 11) provided therein. The rings 120 have a series of resilient fingers 122 extending radially inwardly and angularly outwardly away from the first retention member 110 for resilient gripping engagement with a corresponding abutment provided on a severable indicia element. The rings 120 may be made of spring steel and the fingers formed by slitting such that provide a one-way slide-lock to prevent axial withdrawal of the severable element in the installed position.

As shown, the hinge plate member 106 then, in turn, pivotally mounts a latch plate member 130 which is cutout, as 132, to pivotally receive the hinge plate member 106 therethrough. The latch plate member 130 is pivoted adjacent the middle of the hinge plate member 106 by a pair of pivot pins 136 which are mounted in support blocks 138 and 140 provided on each of the respective plates 106 and 130. In this form, a coiled spring 142 is mounted on each of the pins 136 and has a tang finger 144 secured to the hinge pin 135 such that when the hinge plate member 106 is pivoted in a counter-clockwise direction (FIG. 8), it moves against the bias of the spring and upon release of the hinge plate member, it springs-up into the dotted line position illustrated in FIG. 8. Similarly, the springs 142 are wound such that when the hinge plate member 106 is pivoted in a counter-clockwise position (FIG. 8), it acts to pivot the latch plate member 130 in the opposite or clockwise direction. Accordingly, there is provided a double-pivot 135 and 138 for the hinge plate and latch plate members 106 and 130, respectively.

Figure 8:
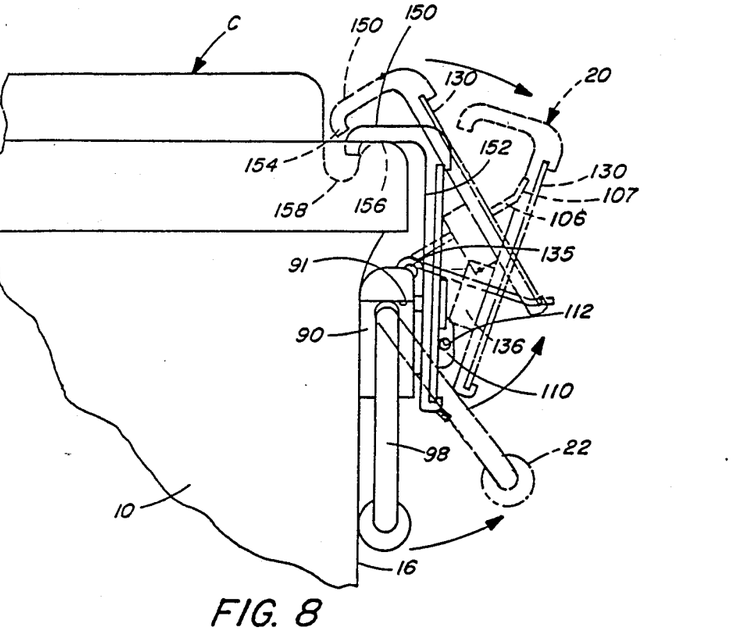
FIG. 8 is a fragmentary, generally schematic illustration of the operation of one of the latch mechanism in accordance with the present invention.

As best seen in FIGS. 5 and 8, the latch plate member 130 includes a generally inverted, J-shaped clamp portion 150 which extends outwardly and inwardly from a linear portion 152. The clamp portion 150 includes a terminal hook-like end portion 154 adapted to be received in clamping relation over the peripheral curved flange 156 defined by a generally S-shaped recessed groove 158 formed in the cover member C. Accordingly, as will be seen in FIG. 8 the support bar member 90 acts to space the linear portion 152 of the latch plate member 130 outwardly so that it is in general parallel alignment with a confronting sidewall of the case so as to maximize the holding power of the latch mechanism in the closed condition thereof.

In the latch mechanism, the spacer bar 90 acts to hold the hinge plate member 106 generally parallel to the sidewall 16 of the case. The piano pivot (point) hinge 135 (FIG. 8) is disposed in general parallel alignment with the outer edge of the flange 156 of the cover member and the hook-like end portion 154 thereof is laterally off-set inwardly of the pivot 135 whereby the hinge plate member 106 is pivoted downwardly and the latch plate member 130 is simultaneously pulled downwardly (clockwise) and inwardly so as to draw the clamp portion 150 downwardly and outwardly relative to the S-shaped flange until the hinge and latch plate members 106 and 130 are in a generally parallel relation and ready for securement via the severable indicia element. In this position, the passageways 112 and 118 in the retention members 110 and 106 are exposed (FIG. 8) and in axial alignment with one another so as to slidably receive the severable indicia element for locking the cover member in a closed condition relative to the open top of the case, as will hereinafter be more fully described.

In FIGS. 4 and 5, it will be seen that the S-shaped flange 156 which defines the outer peripheral edge of the cover member C and provides a peripheral seat 170 so as to receive a resilient seal of polymeric material 172 in the form of a gasket to provide a seal in the closed condition of the cover member C. This construction provides a compression groove for locking the cover member C to the case.

Now in the invention, a severable indicia element 151 is provided to give a tamper-evident lock condition. In one form, the indicia element 151 may have an arrow-shaped configuration including an elongated body portion 157 with a generally pointed head portion 155 at one lead end, and an enlarged feather-like portion 157 at the opposite end. The body portion 153 has a reduced dimension (weakened) neck-like portion 159 disposed adjacent the pointed head portion 155 and an enlarged dimension portion 160 which has generally the same transverse dimension as the body portion 153. The portion 160 is made integral with a generally conical abutment portion 162 which tapers downwardly and inwardly in a direction toward the pointed end portion 155. This conical portion 160 has a maximum transverse dimension which is greater than the corresponding transverse dimension of the body portion 151 and 160 so as to provide an abutment or stop to prevent axial withdrawal of the indicia element in the installed position thereof.

Indicia element 151 is preferably made from a polymeric material and incorporates a heat sensitive material disposed, for example, on the feather-like end portion to provide an automatic indication as to whether or not the case and hence, the medical instrument contained therein, have been adequately processed to achieve the desired sterilization. Typically, this sterilization would be carried out in an autoclave in a manner known in the art. In the invention, the indicia element may be dip-coated or painted with a heat sensitive ink composition or such color indicator may be provided by means of a strip containing such a heat sensitive ink composition. For example, the indicia element could be made from a white polymeric composition for use in a steam processing application and from a yellow composition for a gas processing application, and wherein the feather-like portion would turn from white or yellow to a brown color upon heat activation of the chemical ink composition to indicate that the case has been sterilized by processing with either steam or gas.

In a preferred form, the ink composition may be dip-coated with a sterilization indicator ink commercially available under the trade designations S-FWC-566-D and G-FYC-369-C from Tempil Incorporated by New Jersey. Accordingly, in the invention it will be recognized that the indicia element may be of any configuration and/or size so long that it is able to structurally function to carry out the intended purpose of the tamper-evident lock feature, and also such that it can provide the visual color variation to indicate the sterilized condition of the case.

In the invention, the body and cover members of the case are preferably made from an annodized aluminum material which has been hard coated so as to provide a lightweight construction which can be competitively constructed and which is generally scratch resistant. Both the bottom and top of the case are of a rivetless construction so as to minimize corrosion and facilitate cleaning maintenance of the case. The latch mechanism is of a double-pivot action so as to maximize the leverage for ease in closing the cover member.

In operation, when the hinge plate member 106 is in the closed position the indicia element 151 is inserted pointed end first through the passageway 112 and 118 in the retention members 110 and 116 (FIG. 8). In this position, the reduce transverse dimension portion 159 of the indicia element is generally aligned with the perpendicular surface 114 (FIG. 7) of the retention member 116 such that when the latch plate member 106 is pivoted upwardly about the pivot point 135, the reduced dimension portion 159 is severed (sheared) off such that the hinge plate member 106 is then allowed to be manually pivoted upwardly against the resilient bias force of the springs 142, as foresaid. Thus severed, the indicia element can then be withdrawn from the retention members 110 and 116 and a new indicia element inserted for the next succeeding operation.

Figure 12:
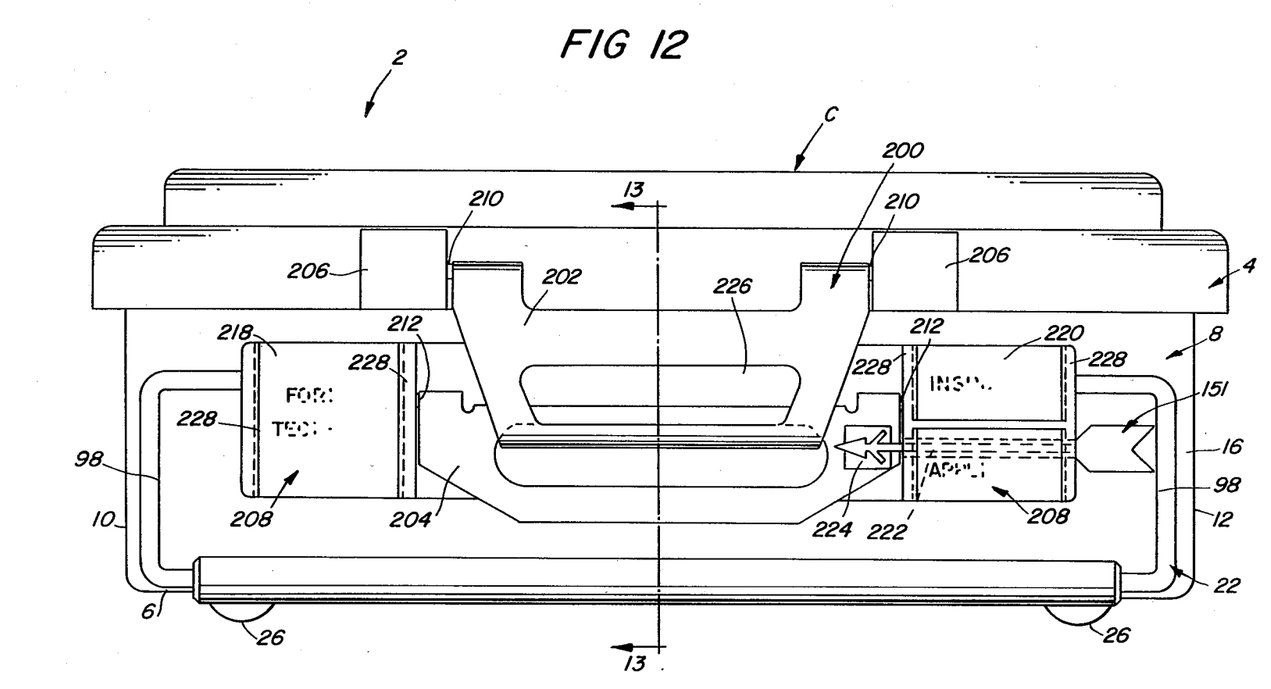
FIG. 12 is an end elevational view of the case in accordance with a second preferred embodiment of the present invention.

A second preferred embodiment of the medical sterilizer device with improved latch mechanism in accordance with the present invention is illustrated in FIGS. 12-16. Like numerals will be used in the second embodiment to represent like elements from the first embodiment. Sterilizer device 2 includes cover member C which is detachably and lockably secured to case 4 by a pair of oppositely disposed "double-action" latch mechanisms 200, the latch mechanisms being of substantially identical construction. As seen in FIG. 12, latch mechanism 200 includes cover latch plate 202 hingedly connected, as at 210, to cover member C through support bar member 206. Similarly, bottom latch plate 204 is hingedly connected, as at 212, to sidewall 8 through bottom support bar member 208. The hinges may be spring-loaded to faciliate ease of releasing the latches, the operation of which being further discussed below.

Figure 13:
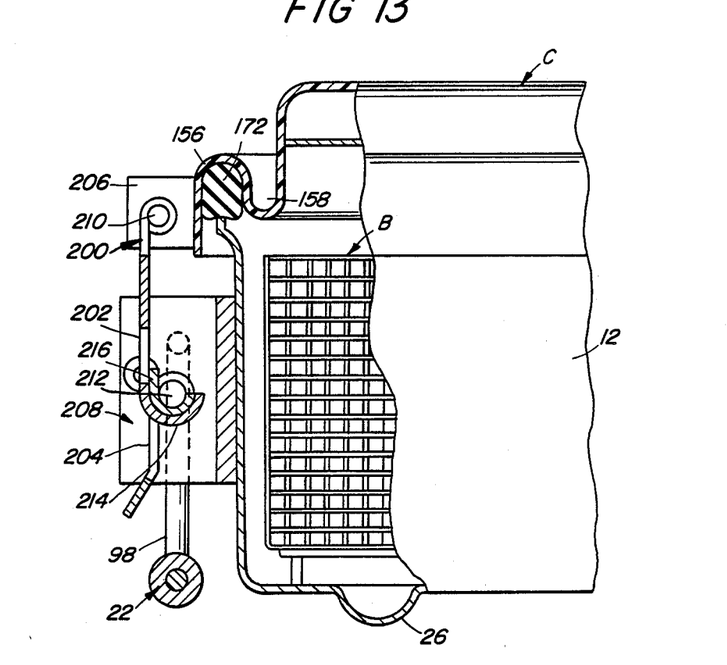
FIG. 13 is a fragmentary, generally schematic view of the operation of one of the latch mechanisms taken along the line 13—13 of FIG. 12.
Figure 14:
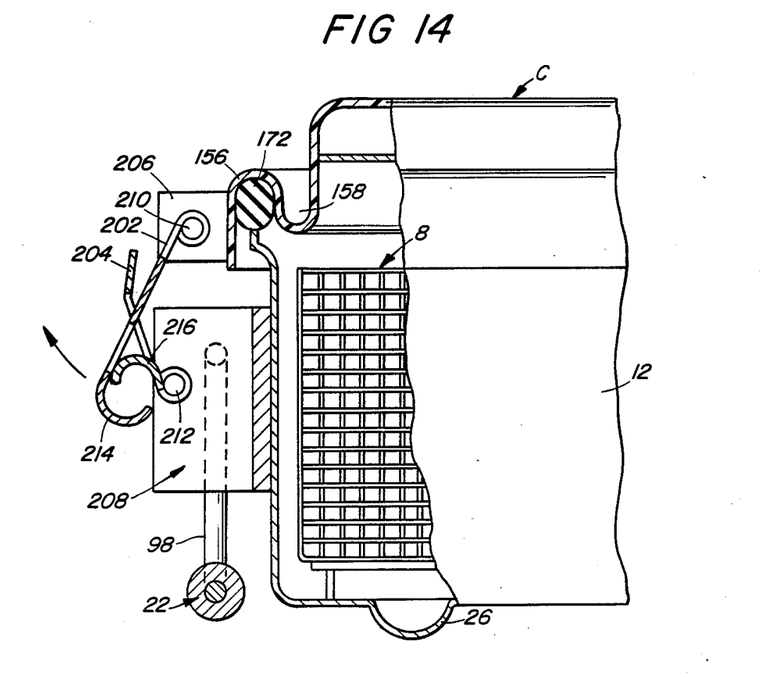
FIG. 14 is a fragmentary, generally schematic view of the operation of the latch mechanism of the case illustrated in FIG. 12.
Figure 15:
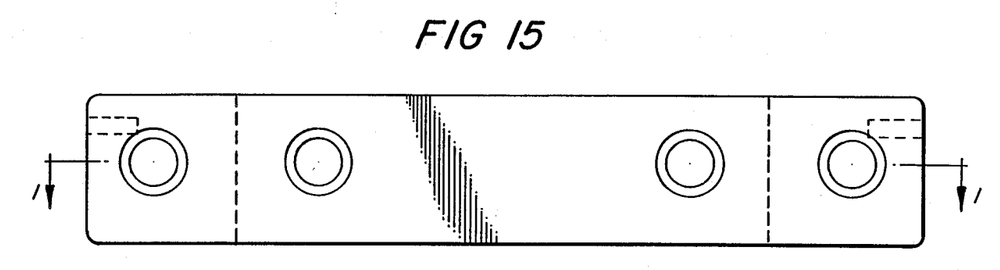
FIG. 15 is a plan view of the bottom support bar member of the embodiment shown in FIG. 12.
Figure 16:
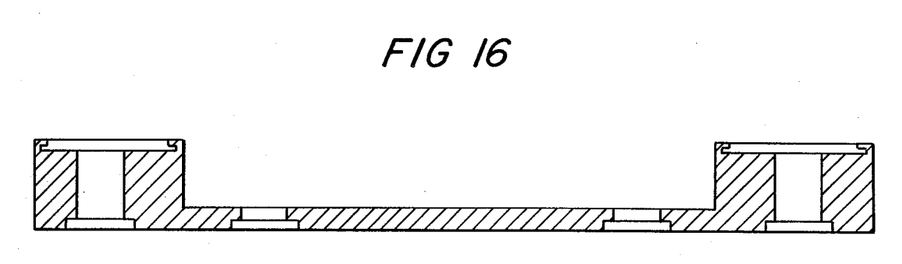
FIG. 16 is a vertical sectional view taken along line 16—16 of FIG. 15.

As best illustrated in FIGS. 13 and 14, cover latch plate 202 is preferably, substantially J-shaped, with the inwardly extending curved portion 214 forming the lower edge of the plate opposite the pivot axis. Bottom latch plate 204 has a hook portion 216. Hook portion 216 of the bottom latch plate is configured to engage with curved portion 214 of the cover latch plate when the bottom latch plate is rotated downwardly about its pivot axis and, thus, the latch plates secure the cover in a locked position with the case. This construction of the latch plates provides for increased compression of the resilient seal 172 during the latching operation and, hence, provides a tighter, more air-tight seal then previously used latch mechanisms. Additionally, since the plates lie substantially flat against the sidewall of the case, there is less chance of sterile gown contamination, for example, by a scrub nurse removing the basket. Indicia element 151 is inserted in guide slot 222 formed in bottom support bar member 208. An indicia element trap or hole 224 is formed in one side of the bottom latch plate adjacent the guide slot. When the head and barbs of the indicia element extend into the trap to hold the latch plates in their normally closed position, the barbs expand and the indicia element cannot be removed without being severed by the rotary motion of the plate with respect to the indicia element within the fixed guide slot. Thus, as in the first embodiment, the indicia element provides an indication that the sterilizer seel has been broken and the contents of the case contaminated.

Bottom support bar member 208 may be formed of data card block 218 and identification card block 220. Both blocks 218, 220 have slots 228 for accomodating an information card which allows the operator and subsequent users to identify the contents of the case, without breaking the seal and contaminating the contents. Further, cover latch plate 202 is preferably formed with longitudinal slot 226. Slot 226 provides a space for the operators to insert their fingers to make it easier than opening the latch. The slot also provides a convenient carrying handle for the cover.

In operation, to lock the latches, the user rotates the bottom latch plate downwardly, engaging the upper latch plate, and inserts the indicia element. To open the latch, the user slips his fingers behind the bottom latch plate and pulls the plate outwardly and upwardly, severing the indicia element. The motion of the bottom latch plate causes the cover latch plate to pivot upwardly and the two latch plates disengage. The cover latch plate is spring-loaded and automatically swings outwardly to a convenient position of the user to easily grasp and lift the cover off of the case.

Other advantages and objects of the present invention are encompassed within the appended claims.

We claim:

1. In a sterilization container of the type for use in the sterilization and storage of medical instruments or the like in which the container includes a container body member defined by a bottom and a sidewall and being open at the top, a cover member detachably and lockably attached to the body member for closing the open top of the container body member, the improvement comprising:

a pair of opposed latch mechanisms adapted to releasably secure said cover member in sealed relation with said container body member;

a pair of support bar members fixed to opposite sidewalls of said container body member for mounting said latch mechanisms to said container;

each of said latch mechanisms including a hinge plate member and a latch plate member;

said hinge plate member pivotally fixed to and cantilevered from said support bar member so that said hinge plate member is spaced from the container sidewall, said hinge plate member having a retention member having an axial passageway extending therethrough;

said latch plate member pivotally mounted to said hinge plate member by a pair of spaced pivot pins;

spring bias means connected between said pivot pins so that when said hinge plate member is pivoted in one direction, said hinge plate member moves against the bias of said spring bias means and pivots said latch plate member in a direction opposite from one said direction;

said hinge plate member and said latch plate member being configured to lockingly engage each with the other when said hinge plate member is pivoted in one direction to thereby lock said cover member in sealed relation with said container body and configured to disengage when said hinge plate member is pivoted in a direction opposite said one direction to thereby unlock said cover member and permit its removal;

a severable indicia element adapted to be disposed in said retention member of said hinge plate member, said indicia element being automatically severed upon actuation of said latch mechanism so as to evidence opening of said container.

2. A sterilization container in accordance with claim 1, wherein the sidewall of said container body is free of any openings and is interiorly formed so as to provide a pair of opposite disposed interior shoulder portions, the associated retention plate member having a pair of integral, oppositely disposed resilient flanges which extend upwardly and outwardly from the general plane of said retention plate member with one of said flange portions being insertable under one of said shoulder portions, the other of said flange portions having a cam-lock lever pivotally mounted thereon and adapted to be pivotally inserted in camming relation under the other of said plate member against the bottom of said container body member.

3. A sterilization container in accordance with claim 1, including a protective inner-plate member disposed between the bottom of said container body and the associated of said retention plate members, said protective inner-plate member having a plurality of apertures oriented in a staggered pattern so as to provide a blocking relationship with the apertures in said cover member thereby to prevent spillage into the interior of said container and puncture of said barrier layer material.

4. A sterilization container in accordance with claim 1, wherein said cover member includes an integral, peripheral skirt-like flange portion formed from the material thereof, said flange portion being formed to provide a first generally U-shaped groove and a second generally inverted U-shaped groove, a flexible gasket member disposed in said second generally inverted U-shaped groove and providing a fluid seal with the corresponding upper peripheral edge defined by the endless sidewall of said container body.

5. A sterilization container in accordance with claim 1, wherein said body member is of a unitary construction with said endless sidewall being free of any openings to to the interior of said container, said sidewall being formed with a pair of oppositely disposed interiorly extending shoulder portions, a perforated retention plate member detachably and resiliently disposed against the confronting bottom surface of said container body member by said shoulder portions, and a cam-lock lever pivotally mounted on said retention plate member adjacent one of said shoulder portions for pivotal cam-action locking engagement under the confronting surface of the respective shoulder portion for holding said retainer plate member in a resilient biased relation against the confronting surface of the bottom of said container body member.

6. A sterilization container as in claim 1 wherein said latch plate member comprises a substantially inverted J-shaped clamp portion adapted to engage said cover member and said hinge plate member has a hook portion for engaging said J-shaped clamp portion, the outer end of said J-shaped clamp portion being laterally offset inwardly of the pivot connection between said hinge plate member sand said latch plate member.

7. A sterilization container of the type for use in the sterilization and storage of medical instruments or the like, said container comprising;
   a body member defined by a bottom and an endless sidewall, said body member being open at the top;
   a cover member for closing the open top of said body member;
   a pair of opposed double-action latch mechanisms adapted to lockably and detachably secure said cover member in sealed relation with said body member, each of said latch mechanisms having a cover latch member hingedly connected to a support bar fixed to said cover member and a body latch member hingedly connected to a support bar fixed to said sidewall of said container body, said support bars laterally spacing said cover latch member and body latch member from said respective cover member and body member;
   said cover latch member being substantially J-shaped and having an inwardly extending curved portion forming the lower edge of said cover latch member;
   said body latch member having a hook portion, said hook portion configured to engage with said curved portion of said cover latch member when said body latch member is pivoted downwardly and thereby sealingly and lockingly secured said cover member to said body member;
   at least one of said latch mechanisms including a severable indicia element adapted to be diposed between said container body member and the associated one of said latch mechanisms after said container has been closed and sealed, said indicia element being automatically severed upon actuation of said associated latch mechanism so as to evidence opening of said container.

* * * * *